(12) United States Patent
Wang et al.

(10) Patent No.: US 8,178,466 B2
(45) Date of Patent: May 15, 2012

(54) DEHYDROCHLORINATION OF HYDROCHLOROFLUOROCARBONS USING PRE-TREATED ACTIVATED CARBON CATALYSTS

(75) Inventors: Haiyou Wang, Amherst, NY (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/007,026

(22) Filed: Jan. 14, 2011

(65) Prior Publication Data

US 2011/0112339 A1 May 12, 2011

Related U.S. Application Data

(62) Division of application No. 12/187,887, filed on Aug. 7, 2008, now Pat. No. 7,884,254.

(60) Provisional application No. 60/963,913, filed on Aug. 8, 2007.

(51) Int. Cl.
| | |
|---|---|
| *B01J 21/18* | (2006.01) |
| *C01B 31/00* | (2006.01) |
| *C01B 31/02* | (2006.01) |
| *C01D 3/00* | (2006.01) |
| *C07C 17/25* | (2006.01) |
| *C07C 19/08* | (2006.01) |
| *C09C 1/56* | (2006.01) |

(52) U.S. Cl. .................... 502/180; 423/414; 423/445 R; 423/449.3; 423/460; 570/156; 570/226; 570/227

(58) Field of Classification Search .................. 502/180; 423/460, 414, 445 R, 449.3; 570/156, 226, 570/227

See application file for complete search history.

(56) References Cited

U.S. PATENT DOCUMENTS

| 2,201,050 | A | * | 5/1940 | Oberle | 423/449.2 |
|---|---|---|---|---|---|
| 3,240,834 | A | | 3/1966 | Kruse et al. | |
| 3,778,387 | A | * | 12/1973 | Urbanic et al. | 502/401 |
| 4,083,801 | A | * | 4/1978 | Das | 502/426 |
| 5,021,164 | A | | 6/1991 | Gay | |
| 6,066,589 | A | * | 5/2000 | Malentacchi et al. | 502/185 |
| 6,284,213 | B1 | | 9/2001 | Paparatto et al. | |
| 6,566,567 | B2 | | 5/2003 | Ahn et al. | |
| 2002/0107421 | A1 | | 8/2002 | Ahn et al. | |
| 2005/0070746 | A1 | | 3/2005 | Tung et al. | |
| 2006/0154810 | A1 | * | 7/2006 | Zhang et al. | 502/180 |
| 2007/0197842 | A1 | | 8/2007 | Mukhopadhyay et al. | |

FOREIGN PATENT DOCUMENTS

| CN | 1436591 | * | 8/2003 |
|---|---|---|---|
| JP | 2006193437 A | | 7/2006 |
| KR | 10-2002-0045235 A | | 6/2002 |
| KR | 10-2002-0049217 A | | 6/2002 |
| KR | 10-2005-0001141 A | | 1/2005 |
| WO | 2007056194 A1 | | 5/2007 |
| WO | 2007079413 A2 | | 7/2007 |
| WO | 2009/021154 | * | 2/2009 |

* cited by examiner

*Primary Examiner* — Patricia L Hailey
(74) *Attorney, Agent, or Firm* — Bruce Bradford

(57) ABSTRACT

The present disclosure provides methods for pre-treating activated carbon before it is used in a dehydrochlorination process. The methods can comprise mixing the activated carbon with an acid, an oxidizing agent in a liquid phase, or an oxidizing agent in a gas phase. Activated carbons undergoing one or more of these methods can exhibit improved stability during the dehydrochlorination process.

15 Claims, 5 Drawing Sheets

DEHYDROCHLORINATION OF HYDROCHLOROFLUOROCARBONS USING PRE-TREATED ACTIVATED CARBON CATALYSTS

CROSS REFERENCE TO RELATED APPLICATION

This application is a Divisional of U.S. application Ser. No. 12/187,887, filed Aug. 7, 2008 (now U.S. Pat. No. 7,884,254) and also related to, and claims priority to, U.S. Application No. 60/963,913, filed Aug. 8, 2007, the disclosures of which are incorporated herein by reference.

BACKGROUND

1. Field of the Disclosure

The present disclosure relates to a method for using activated carbons in dehydrochlorination processes. More specifically, the present disclosure relates to a method for preparing hydroflouoroalkenes from hydrochlorofluoroalkanes using pretreated activated carbon.

2. Description of the Related Art

Activated carbons can be used as a catalyst for the dehydrochlorination, or conversion of hydrochlorofluorocarbons (HCFCs) into fluorinated alkenes that have lower global-warming potentials (GWP). These fluorinated alkenes can be used in a wide variety of applications, including as refrigerants, propellants, cleaning agents, and as monomers of macromolecule compounds.

The activated carbon tends to become deactivated quickly, however, which results in a drastically reduced rate of conversion of the HCFCs. Thus, there is a need for a method or process to improve the stability of activated carbon during the dehydrochlorination process.

SUMMARY OF THE INVENTION

Applicants have found demineralizing and/or oxidizing an activated carbon catalyst unexpectedly stabilizes the catalysts during certain dehydrochlorination reactions, for example, dehydrochlorinating 1,1,1,2-tetrafluoro-2-chloropropane (HCFC 244bb) to form 2,3,3,3-tetrafluoropropene (HFC-1234yf).

Accordingly, in certain aspects of the invention provided is a method for producing a fluorinated alkene comprising dehydrochlorinating a hydrofluorochloroalkane in the presence of a stabilized catalyst, wherein said stabilized catalyst is selected from the group consisting of demineralized activated carbon, oxidized activated carbon, or a combination thereof.

In another aspect of the invention, provided is a method for pre-treating an activated carbon catalyst comprising demineralizing said activated carbon catalyst and oxidizing said activated carbon catalyst.

In yet another aspect of the invention, provided is an activated carbon catalyst prepared according to such a pre-treatment process.

DETAILED DESCRIPTION OF PREFERRED EMBODIMENTS OF THE INVENTION

Figure 1:
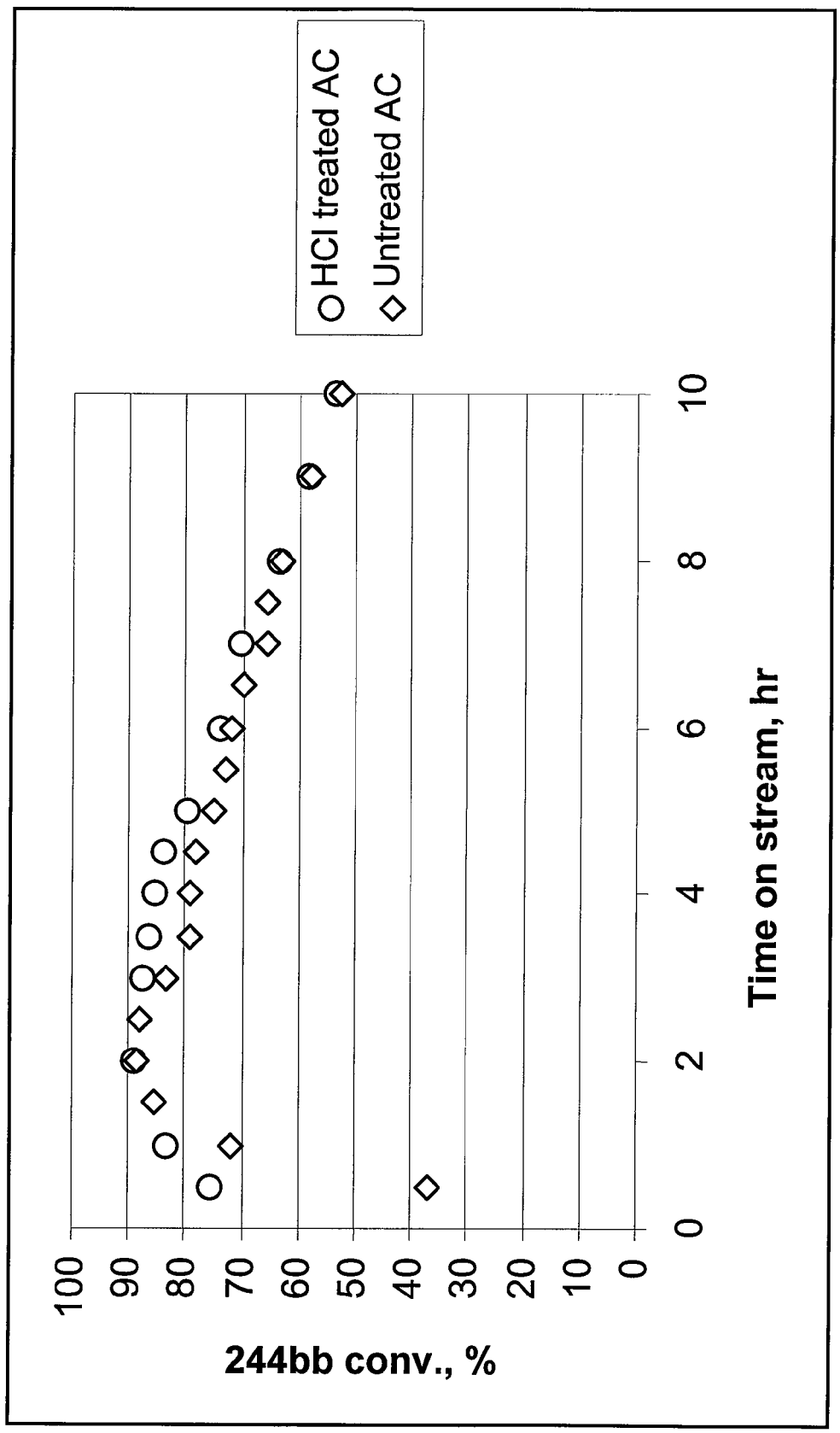
FIGS. 1-5 show experimental data concerning several embodiments of the method of the present disclosure.

The present disclosure has advantageously discovered a novel method for improving the stability of activated carbon (AC) during the dehydrochlorination of HCFCs having at least one hydrogen and at least one chlorine on adjacent carbons. The AC can be pre-treated before being utilized in the dehydrochlorination process according to the methods discussed in greater detail below. As is shown in the provided data, this pre-treatment provides a substantial improvement in the stability and performance of the AC.

In a first embodiment, the AC is pre-treated with an acid at room temperature or higher. Preferred acids for this process include hydrochloric acid (HCl), hydrofluoric acid (HF), or a combination of the two. The pre-treatment with the acid comprises the following steps: 1) the AC is mixed with an aqueous solution of the acid, 2) the suspension is stirred for at least a first period of time at room temperature or higher and then filtered to separate the acid from the AC, 3) the AC is washed with distilled water until substantially free of ions from the acid, and 4) the AC is dried for at least a second period of time at a first temperature. The AC sample can be dried in air at a temperature of about 50° C. to about 120° C., or higher. The AC can also be dried in air at a temperature of about 100° C. to about 110° C. The first period of time can be from about 0.5 hours to about 24 hours, or longer. The second period of time can also be from about 0.5 hour to about 24 hours, or longer.

In a second embodiment, the pre-treatment of the AC can be carried out using an oxidizing agent in a liquid phase. In this embodiment, the pre-treatment comprises the following steps: 1) the AC is mixed with an aqueous solution of the oxidizing agent; 2) the suspension is stirred for at least a third period of time at room temperature or higher and then filtered to separate the AC from the oxidizing agent, 3) the AC is dried for at least a fourth period of time at a second temperature, and then 4) heat-treated in an inert gas, such as nitrogen, for at least a fifth period of time and at a third temperature. The third and fourth periods of time can also be from about 0.5 hour to about 24 hours, or longer. In step 3), the AC can be dried at about 50° C. to about 120° C., or higher. In step 4), the fifth period of time can be about from about 0.5 hour to about 4 hours, or longer. The third temperature can be from about 250° C. to 750° C. or higher. The third period of time can also be 1 hour, and the third temperature can also be about 400° C. For the liquid phase, non-limiting examples of the oxidizing agent include nitric acid ($HNO_3$) and hydrogen peroxide ($H_2O_2$) aqueous solutions, or combinations of the two.

In a third embodiment, the pre-treatment of the AC can be carried out using an oxidizing agent in a gas phase. In this embodiment, the pre-treatment comprises the following steps: 1) the AC is loaded into a reactor, 2) pure or diluted gaseous oxidizing agent is flowed through the reactor, and 3) at least a portion of the AC is oxidized for a sixth period of time at a fourth temperature. In step 2, the oxidizing agent can be diluted with an inert gas, such as nitrogen. The concentration of the oxidizing agent in this diluted mixture can be from about 1% to about 10%. In step 3), the sixth period of time can be from about 5 seconds to about 12 hours or longer, or alternatively, about 2 hours. The fourth temperature can be from about 250° C. to about 750° C., or higher. The fourth temperature can also be about 450° C. Generally speaking, a longer period of time is needed for a lower temperature. During this oxidation step, oxygen-containing groups are formed on the surface of the AC, and a small fraction of the AC may be burned off at elevated temperatures due to deep oxidation. For the gas phase, non-limiting examples of the oxidizing agent include diatomic oxygen ($O_2$) and carbon dioxide ($CO_2$), or combinations of the two.

The AC can be pre-treated with any one of the above described pre-treatments singly, or can be treated with any combination of the three. For example, the AC can be pretreated with HCl, followed by a second pre-treatment with HNO$_3$. In addition, although the above-described methods concern AC that is pre-treated before being used in a dehydrochlorination process, the present disclosure also contemplates treating spent or deactivated AC with these methods, to rejuvenate the AC. The deactivated AC can undergo the treatment methods described above, and then be used in a dehydrochlorination process once they have been rejuvenated.

There are a number of HCFCs that can be used in the dehydrochlorination process of the present disclosure. Table 1 below shows a list of possible HCFCs and the resulting fluorinated alkenes that are produced by the dehydrochlorination process.

TABLE 1

| HCFC | Fluorinated alkenes |
|---|---|
| CF$_3$CFClCH$_3$ (244bb) | CF$_3$CF=CH$_2$ (1234yf) |
| CF$_3$CHFCH$_2$Cl (244eb) | CF$_3$CF=CH$_2$ (1234yf) |
| CF$_3$CH$_2$CHFCl (244fa) | CF$_3$CH=CHF (trans/cis-1234ze) |
| CF$_3$CHClCH$_2$F (244db) | CF$_3$CH=CHF (trans/cis-1234ze) |
| CF$_3$CFClCH$_2$F (235bb) | CF$_3$CF=CHF (Z/E-1225ye) |
| CF$_3$CHFCHFCl (235ea) | CF$_3$CF=CHF (Z/E-1225ye) |
| CF$_3$CH$_2$CF$_2$Cl (235fa) | CF$_3$CH=CF$_2$ (1225zc) |
| CF$_3$CHClCHF$_2$ (235da) | CF$_3$CH=CF$_2$ (1225zc) |
| CF$_3$CFClCHF$_2$ (226ba) | CF$_3$CF=CF$_2$ (1216) |
| CF$_3$CHFCF$_2$Cl (226ea) | CF$_3$CF=CF$_2$ (1216) |

In any of the above-described embodiments, the HCFC that undergoes dehydrochlorination can be 1,1,1,2-tetrafluoro-2-chloropropane, also known as 244bb, and the resultant fluorinated alkene is 2,3,3,3-tetrafluoropropene, also known as 1234yf. The following experimental data demonstrates that pre-treatment of AC, before being used in the dehydrochlorination process, can improve the ability of the ACs to catalyze the conversion of HCFCs into fluorinated alkenes, over that which is achieved with untreated AC. Methods of dehydrochlorination are described in co-pending U.S. patent application Ser. No. 11/619,592, filed on Jan. 3, 2007, (hereinafter "the '592 application") which is incorporated herein by reference. The AC is available from a number of sources, including the Alfa Aesar Corporation.

Example 1

244bb Dehydrochlorination Over Untreated and HCl-Treated ACs

In Example 1, untreated and HCl-treated activated carbons (ACs) were used as dehydrochlorination catalysts. 20 cc of catalyst granules was used. A mixture of 92.7% of 244bb/6.5% of 1233xf was passed through a bed of each of the AC catalysts at a rate of 6 g/h. 1233xf is an intermediate product formed during the fluorination of CCl$_2$=CClCH$_2$Cl, and is used as raw material for producing 244bb, as described in the '592 application. For this reason, streams of 244bb often comprise some amount of 1233xf. The temperatures at the bottom of the catalyst bed and at the top of catalyst bed were recorded and reported. As shown in FIG. 1, which shows data at 350-385° C., the stability of AC was slightly improved after treatment with HCl.

Example 2

244bb Dehydrochlorination Over HCl- and HCl & HNO$_3$-Treated Activated Carbons

Figure 2:
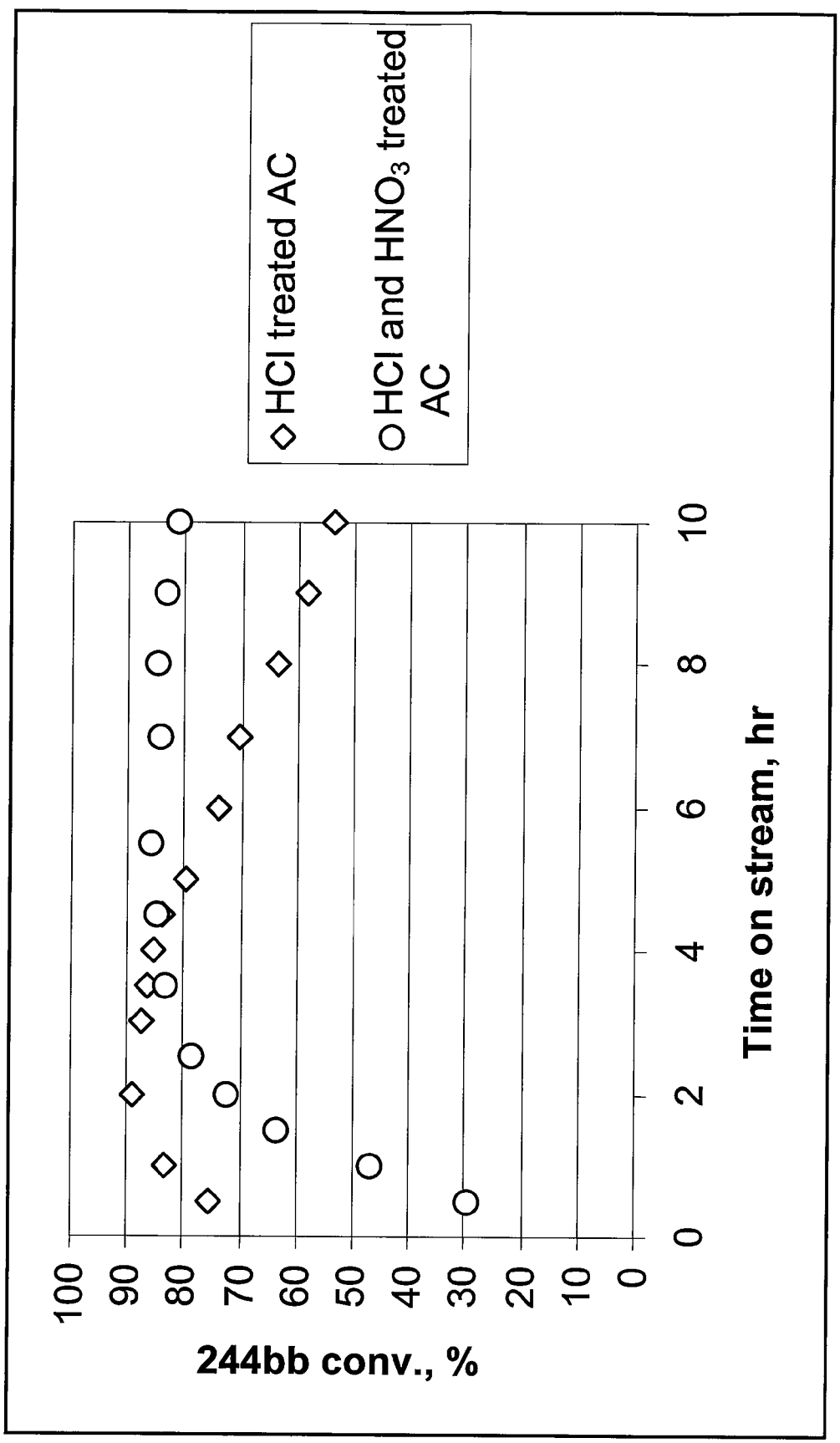

In Example 2, AC pretreated with HCl, and AC pre-treated with both HCl & HNO$_3$, according to the methods described above, were used as dehydrochlorination catalysts. 20 cc of catalyst granules was used. A mixture of 92.7% of 244bb/6.5% of 1233xf was passed through a bed of each of the AC catalysts at a rate of 6 g/h. The temperatures at the bottom of the catalyst bed and at the top of catalyst bed were recorded and reported. As shown in FIG. 2, at 350-385° C., compared to the AC pre-treated with only HCl, the HCl & HNO$_3$ pre-treated AC showed much higher stability. Over the latter the conversion of 244bb was still above 80% after 10 hours on stream, while over the former it was already below 55% after 10 hours on stream. This result suggests oxidation treatment in liquid phase with HNO$_3$, particularly when used in conjunction with the pre-treatment of HCl, can greatly improve the stability of AC.

Example 3

Figure 3:
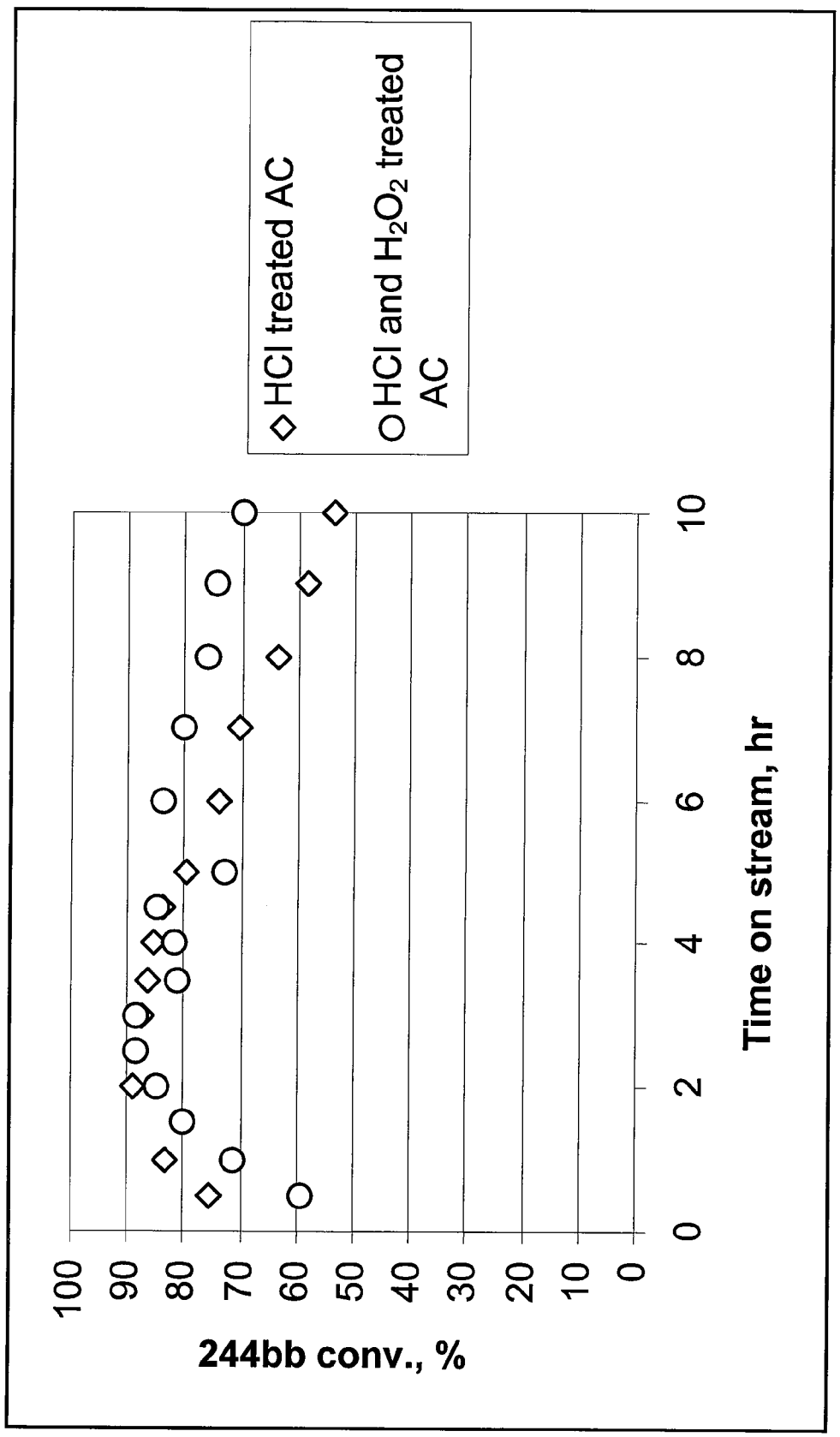

244bb Dehydrochlorination Over HCl- and HCl & H$_2$O$_2$-Treated Activated Carbons In Example 3, AC pre-treated with HCl, and AC pre-treated with both HCl & H$_2$O$_2$, according to the methods described above, were used as dehydrochlorination catalysts. 20 cc of catalyst granules was used. A mixture of 92.7% of 244bb/6.5% of 1233xf was passed through a bed of each of the AC catalysts at a rate of 6 g/h. The temperatures at the bottom of the catalyst bed and at the top of catalyst bed were recorded and reported. As shown in FIG. 3, at 350-385° C., compared to the AC pre-treated with HCl only, the AC pre-treated with both HCl & H$_2$O$_2$ exhibited higher stability. The latter exhibited a rate of conversion of 244bb of about 70% after 10 hours on stream, while the former exhibited a rate of below about 55% after 10 hours on stream. This result suggests that pre-treatment of the AC in liquid phase with H$_2$O$_2$, after pre-treatment with HCl, can improve the stability of the AC over that which is only pre-treated with HCl.

Example 4

Figure 4:
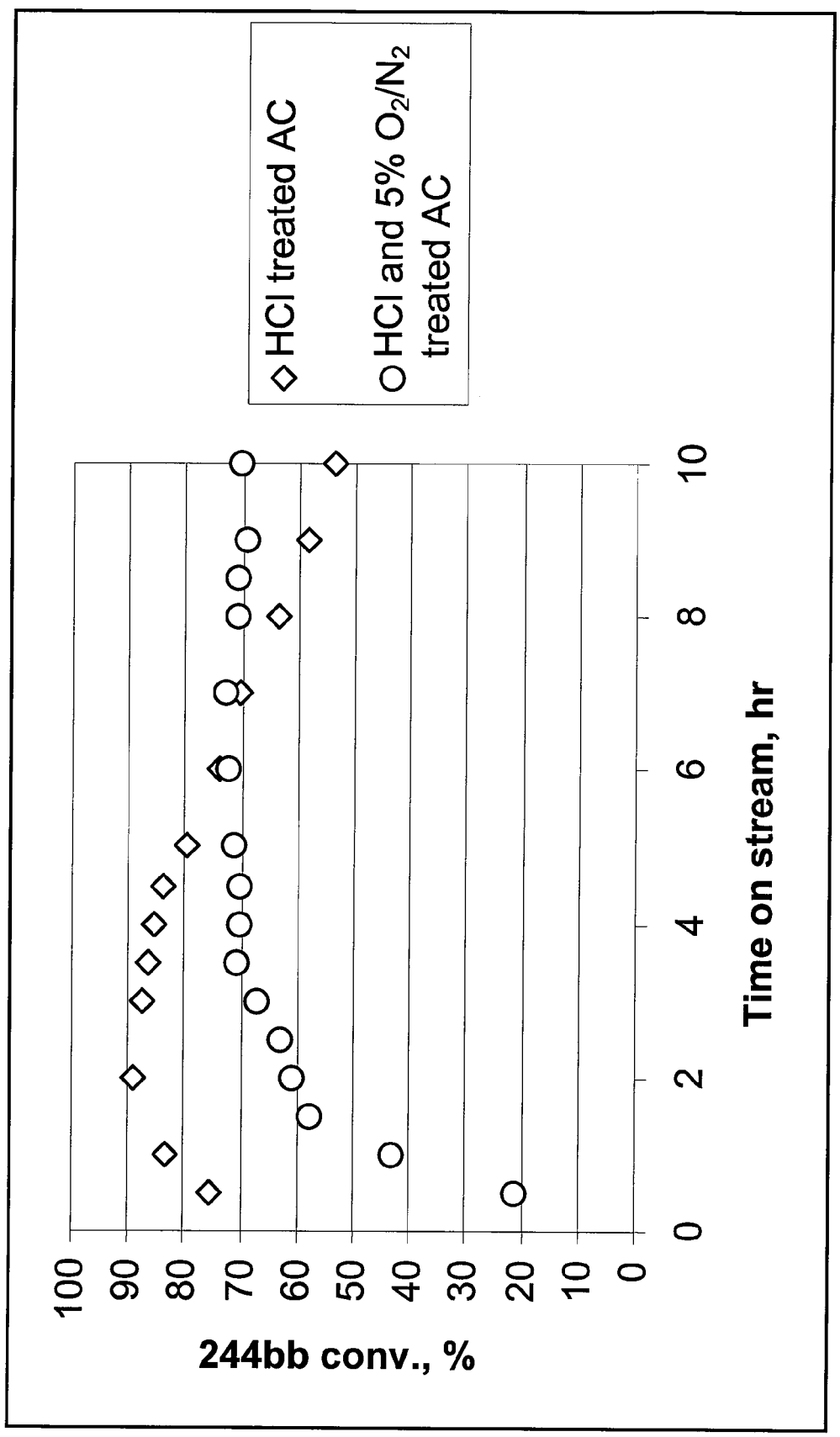

244bb Dehydrochlorination Over HCl- and HCl & 5% O$_2$/N$_2$-Treated Activated Carbons In Example 4, AC pre-treated with only HCl and AC pre-treated with HCl & a mixture of 5% O$_2$/95% N$_2$ were used as dehydrochlorination catalysts. 20 cc of catalyst granules was used. A mixture of 92.7% of 244bb/6.5% of 1233xf was passed through a bed of each of the AC catalysts at a rate of 6 g/h. The temperatures at the bottom of the catalyst bed and at the top of catalyst bed were recorded and reported. As shown in FIG. 4, at 350-385° C., the AC treated with HCl and the mixtures of 5% of O$_2$/95% of N$_2$ was able to maintain its activity at the level of about 70% for almost 7 hours (from the $3^{rd}$ to the $10^{th}$ hours on stream), at least. The performance of the HCl-treated AC, in contrast, decreased over time. This indicates that oxidation pre-treatment of the AC with a gaseous O$_2$ mixture, particularly in conjunction with pre-treatment with HCl, can greatly improve the stability of ACs long term.

Example 5

244bb Dehydrochlorination Over Pristine and HNO$_3$-Treated Activated Carbons

Figure 5:
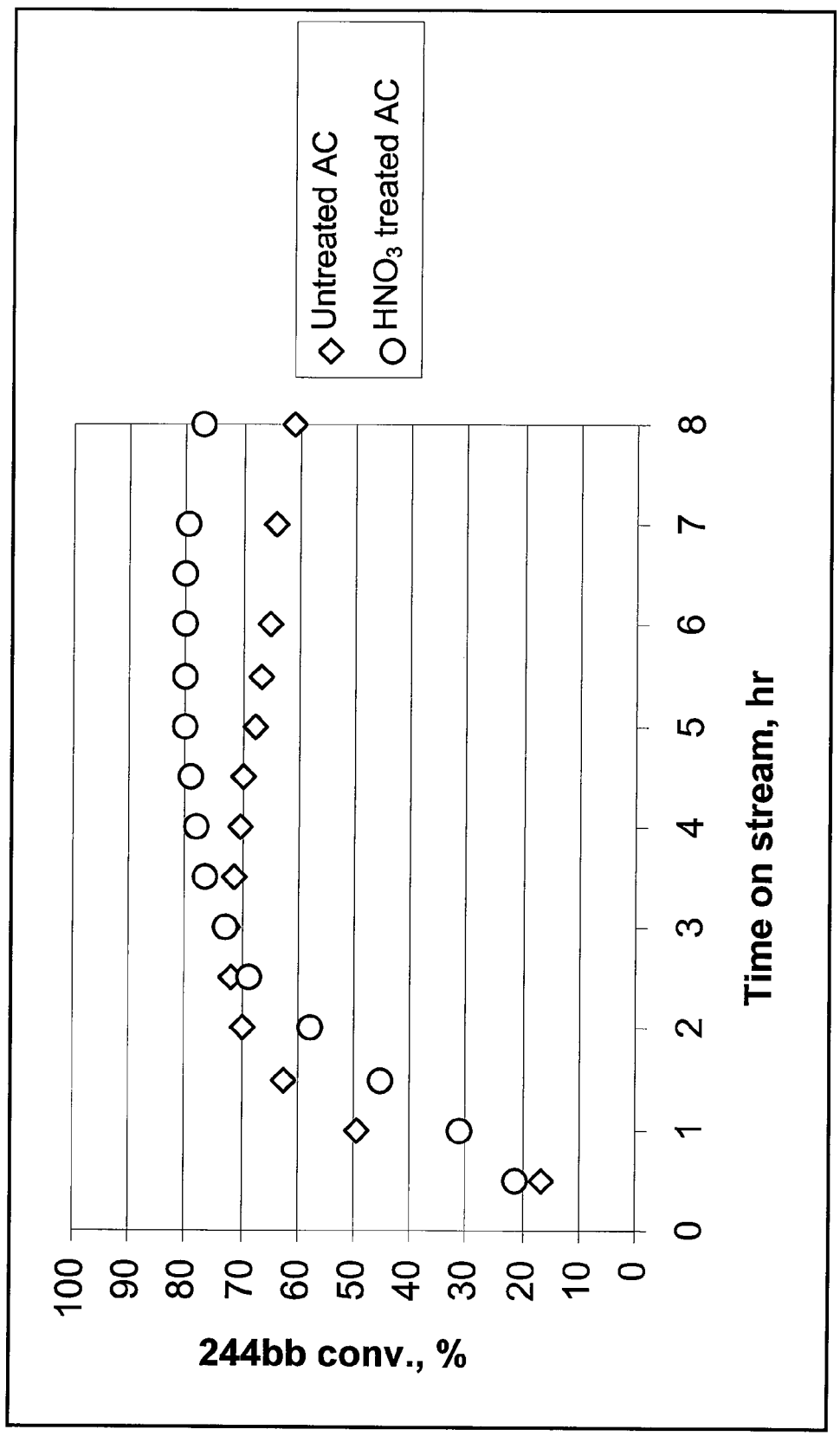

In Example 5, untreated AC, and AC pre-treated with HNO$_3$ according to the method described above, were used as dehydrochlorination catalysts. 20 cc of catalyst granules was used in a typical run. A mixture of 97.2% of 244bb/2.0% of 1233xf was passed through catalyst bed at a rate of 6 g/h. The temperatures at the bottom of the catalyst bed and at the top of catalyst bed were recorded and reported. As shown in FIG. 5, at 350-385° C., the AC pre-treated with $HNO_3$ was able to maintain its activity at the level of above 75% from the 4th to the $8^{th}$ hour. The performance of the untreated AC, by contrast, steadily decreased over time. This indicates that the stability of the AC can be significantly improved by pre-treatment with $HNO_3$, even without pre-treatment with HCl.

The present invention having been thus described with particular reference to the preferred forms thereof, it will be obvious that various changes and modifications may be made therein without departing from the spirit and scope of the present invention as defined in the appended claims.

What is claimed is:

1. A method for pre-treating an activated carbon catalyst consisting essentially of:
   demineralizing said activated carbon catalyst, and
   oxidizing said activated carbon catalyst in the presence of at least one oxidizing agent selected from the group consisting of nitric acid, hydrogen peroxide, $O_2$, $CO_2$ and combinations thereof.

2. The method of claim 1 wherein said demineralizing step comprises contacting said activated carbon catalyst with at least one acid selected from the group consisting of hydrochloric acid and hydrofluoric acid.

3. An activated carbon catalyst prepared according to the process of claim 1.

4. The method of claim 1 wherein the demineralizing step comprises:
   a. mixing the activated carbon catalyst with an aqueous solution of an acid selected from the group consisting of hydrochloric acid, hydrofluoric acid, and combinations thereof;
   b. washing the activated carbon catalyst with water until it is substantially free of ions; and
   c. drying the activated carbon catalyst.

5. The method of claim 4 wherein the activated carbon catalyst is dried at a temperature of about 50° C. to about 120° C.

6. The method of claim 1 wherein said oxidizing agent is provided in a liquid phase.

7. The method of claim 6 wherein said oxidizing step comprises
   a. mixing the activated carbon catalyst with an aqueous solution of an oxidizing agent selected from the group consisting of nitric acid, hydrogen peroxide and combinations thereof;
   b. drying the activated carbon catalyst; and
   c. heat-treating the activated carbon catalyst in the presence of an inert gas.

8. The method of claim 7 wherein the activated carbon catalyst is dried at a temperature of about 50° C. to about 120° C.

9. The method of claim 7 wherein the activated carbon catalyst is heat-treated at a temperature of about 250° C. to about 750° C.

10. The method of claim 7 wherein the inert gas comprises nitrogen.

11. The method of claim 1 wherein said oxidizing agent is provided in a vapor phase stream.

12. The method of claim 11 wherein said oxidizing step comprises contacting the activated carbon catalyst with the vapor phase stream, wherein the oxidizing agent is selected from the group consisting of $O_2$, $CO_2$ and combinations thereof.

13. The method of claim 12 wherein the oxidizing agent is provided within the vapor phase stream at a concentration of about 1 wt % to about 10 wt %.

14. The method of claim 12 wherein the inert gas comprises nitrogen.

15. The method of claim 12 wherein the contacting step is at a temperature between about 250° C. to about 750° C.

* * * * *